United States Patent [19]

Ohyama et al.

[11] Patent Number: 5,756,780
[45] Date of Patent: May 26, 1998

[54] PROCESS FOR THE PREPARATION OF A PURIFIED 3,4-EPOXYCYCLOHEXYL METHYL(METH)ACRYLATE AND, A STABILIZED 3,4-EPOXYCYCLOHEXYL METHYL ACRYLATED

[75] Inventors: Kyuichi Ohyama; Akira Horiguchi, both of Ohtake, Japan

[73] Assignee: Daicel Chemical Industries, Ltd., Sakai, Japan

[21] Appl. No.: 702,140

[22] Filed: Aug. 23, 1996

[30] Foreign Application Priority Data

Sep. 1, 1995 [JP] Japan .................. 7-248452
Sep. 1, 1995 [JP] Japan .................. 7-248453
Sep. 13, 1995 [JP] Japan .................. 7-259557

[51] Int. Cl.⁶ .............. C07D 301/12; C07D 301/32; C07D 303/17
[52] U.S. Cl. ................. 549/541; 549/525; 549/546
[58] Field of Search ................... 549/525, 541, 549/546

[56] References Cited

U.S. PATENT DOCUMENTS 5,382,676  1/1995  Kuwana et al. .................. 549/541

*Primary Examiner*—C. Warren Ivy
*Assistant Examiner*—Lyman H. Smith
*Attorney, Agent, or Firm*—Morgan & Finnegan, LLP

[57] ABSTRACT

Disclosed are an improvement of a process for the preparation of a purified 3,4-epoxycyclohexyl methyl(meth) acrylate, and a stabilized 3,4-epoxycyclohexyl methyl(meth) acrylate.

9 Claims, 1 Drawing Sheet

Figure 1

PROCESS FOR THE PREPARATION OF A PURIFIED 3,4-EPOXYCYCLOHEXYL METHYL(METH)ACRYLATE AND, A STABILIZED 3,4-EPOXYCYCLOHEXYL METHYL ACRYLATED

FIELD OF THE INVENTION

The present invention relates to a process for the preparation of a purified 3,4-epoxycyclohexyl methyl(meth)acrylate. Furthermore, the present invention relates to a stabilized 3,4-epoxycyclohexyl methyl(meth)acrylate.

In particular, the present invention relates to the improvement of a process for the preparation of a purified 3,4-epoxycyclohexyl methyl(meth)acrylate having an excellent stability to coloring for a long time of period.

BACKGROUND OF THE INVENTION

Heretofore, there have been widely known various (meth)acrylate monomers such as methyl(meth)acrylate, ethyl (meth)acrylate, 2-ethylhexyl(meth)acrylate, etc. which are monofunctional monomers, and trimethylolpropane triacrylate, pentaerythritol triacrylate, etc., which are multifunctional monomers.

The (meth)acrylate monomers are useful compounds which can be employed as intermediate materials for a coating composition, and which can be readily polymerized alone or copolymerized with other compounds having an unsaturated-group by heating, irradiation of ultraviolet rays, ionized radiation rays, and radical polymerization initiators.

However, the monofunctional monomers have a disadvantage that an odor of the residual monomer after curing causes a remarkable problem in the case of using as a component of printing ink compositions or coating compositions.

Furthermore, the multifunctional monomers also have a disadvantage that it is necessary to be used in large amounts with respect to resins in the case of using as a diluent of printing ink compositions or coating compositions, resulting in loss of excellent properties of the resins.

In particular, an epoxidized cyclohexenyl methyl(meth)acrylate which has an alicyclic epoxy group capable of being cured by a cation and (meth)acrylic group, that is, 3,4-epoxycyclohexyl methyl(meth)acrylate is exceedingly useful as a polymerizable monomer for polymerizing or copolymerizing.

3,4-epoxycyclohexyl methyl (meth)acrylate is low in viscosity and mild in odor, and has the solubility to resins over a wide range of concentration, and further it is useful as a resin component for ink compositions, coating compositions, adhesive compositions, covering agents and a starting material for molding resins or a modifier thereof.

It is noted that there have been basically known 3,4-epoxycyclohexyl methyl(meth)acrylate and a process for the preparation thereof, and it is specifically prepared by the esterification reaction of tetrahydrobenzyl alcohol with (meth)acrylic acid or by the transesterification reaction of tetrahydrobenzyl alcohol with a (meth)acrylate ester and successively by the epoxidation reaction with a peracid [Batog, A. E.; Zaitsev, S. Yu.; Kiryushima, N. P.; Zaitseva, V. V. (Inst.Fiz.-Org. Khim. Uglechim., Donetsk, USSR). Zh. Org. Khim. 1982, 18(1), 90-4 (Russ)].

The reaction schemes are represented by the following chemical equations;

in the equations, $R^1$ is hydrogen or a methyl group, $R^2$ is an alkyl group].

However, a process for the preparation of a purified, that is, a commercially available 3,4-epoxycyclohexyl methyl (meth)acrylate, has not been disclosed up to date.

In particular, there has not been known such a process that even a waste water treatment is taken into consideration or even a small amount of impurity detected by a heptane test described hereinafter can be removed.

On the other hand, it has been known that 3,4-epoxycyclohexyl methyl(meth)acrylate has a disadvantage of exceedingly readily polymerizing, particularly, through the preparation processes, during being stored and or shipped under the influence by heating and exposing to a photo-energy.

In order to solve the disadvantage, JP-A-2262574 teaches a method for preventing polymerization, which uses quinones, etc. together with phosphorous compounds under the presence of molecular state oxygen gas.

However, it has been found by the present inventors that the effect by the method described hereinabove in which the polymerization inhibitors are used is not sufficient in the case of the preparation processes from a viewpoint of advanced commercial uses.

It is one of reasons why the effect by the method was not sufficient that there were not able to be anticipated sufficient qualities to be possessed in a product of 3,4-epoxycyclohexyl methyl(meth)acrylate, which was not produced on a commercial basis in those days when the JP-A was filed.

Specifically describing, it is required that low boiling ingredients in a commercially available 3,4-epoxycyclohexyl methyl(meth)acrylate must be removed to the extent ranging from 2 to 3%, more preferably, not more than 1%.

For that purpose, it is required that heating temperatures are raised and that a processing time of period is extended in a step of removing the low-boiling-point ingredients.

However, raising up of the temperatures and/or extension of the processing time of period generates, even though minor amounts, the polymers in a product.

It has been found that the polymers in a product cause problems even though such minor amounts through the advanced developments in relation to a commercially available 3,4-epoxycyclohexyl methyl(meth)acrylate.

For example, it is one of the problems that the polymers ooze out as adhesives and insoluble substances in the case of preparing intermediate materials of resins for coatings using 3,4-epoxycyclohexyl methyl (meth)acrylate including the polymers, resulting in causing various problems through processing and in producing coatings having a remarkably spoiled commercial valuation.

It appears that the minor amounts of polymers in a commercially available 3,4-epoxycyclohexyl methyl(meth) acrylate are composed of the polymers of 3,4-epoxycyclohexyl methyl (meth) acrylate itself having a low molecular weight.

The contents of such polymers having a low molecular weight can be shown by weight % with a measuring method using n-heptane or n-hexane, in which 10 g of a product is dissolved in 100 cc of n-heptane or n-hexane and resulting suspensions are filtered and weighed.

It is known that a commercially available 3,4-epoxycyclohexyl methyl (meth) acrylate must exhibit the HT value of not more than 0.1% by weight.

It was found that the method described in JP-A-2262594 alone can provide 3,4-epoxycyclohexyl methyl(meth) acrylate having the polymer contents of more than 0.1% by weight in HT value, more specifically, 0.14% by weight or so, which values are not sufficient in quality, by a recollected confirmation test using HT carried out thereafter.

That is, further more effective methods for inhibiting polymerizing in each step of the preparation processes must be developed in order to produce a purified 3,4-epoxycyclohexyl methyl(meth)acrylate on a commercial basis.

It is to be noted that 3,4-epoxycyclohexyl methyl(meth) acrylate has an alicyclic epoxy group which tends to exceedingly readily react with an organic acid derived from an organic peracid which is an epoxidation agent, for example, the epoxy group reacts with acetic acid derived from peracetic acid in the case of using peracetic acid as an organic peracid, resulting in polymerization of 3,4-epoxycyclohexyl methyl(meth)acrylate and opening of the epoxy group, particularly through an evaporation step.

Accordingly, it is required that an organic acid is removed from a crude reaction solution as early as possible in order to maintain a short time of period contacting with the epoxy group.

Such more effective methods do not have been developed up to date. Furthermore, it is to be noted that, heretofore, various processes for removing the organic acid and organic peracid, for example, (1) a refining process by distillation;

In the case of a heat resistible product, this process has been usually carried out.

(2) a refining process by extraction with water;

The organic acid or organic peracid, which are dissolved in a crude reaction solution, is primarily removed by an extraction with water and successively by distillation, in order to prevent the polymerization or the side reaction of an epoxy compound on distilling the crude reaction solution without any refining processes.

(3) a refining process by neutralization; have been applied.

In the case of incapability of removing the organic acid or organic peracid or in the case that the organic acid in an aqueous solution readily reacts with an epoxy compound, this neutralization process has been usually applied.

Furthermore, in the case of incapability of removing the substances in which the polymerization and the side reaction are caused, by merely adjusting to neutralization point of PH of the solution, the substances are occasionally removed with an aqueous alkali solution.

Distillation is carried out in order to refine after removing the substances by neutralization.

However, the prior art (1) is often incapable of being applied, because it has a disadvantage that there are caused the polymerization or the opening reaction of epoxy groups by distillation alone because of ease in the reaction of epoxy groups with an organic acid.

Furthermore, the prior arts (2) and (3), which are often applied in the case of incapability of applying the prior art (1), are also often incapable of being applied in the case of the rapid reaction velocity of epoxy groups with an organic acid.

Still further, the prior art (3) is often incapable of putting into practice on an industrial basis because of not only large amounts of a product loss but also a considerable load in water treatments.

As mentioned above, the prior arts (1), (2) and (3) include difficult disadvantages, respectively, in the case of applying on an industrial basis.

That is, the prior arts (1), (2) and (3) have been industrially incapable of being applied to an epoxy compound having properties that a crude reaction solution can not be refined by distillation alone because of the polymerization, the side reaction and that an epoxy group tends to rapidly react with an organic acid and or water.

It is to be noted that even though the centrifugal extractor as mentioned above is used in order to remove almost of the organic acid and organic peracid by extracting with water, there can not be removed small amounts of them.

And, there is a disadvantage in a product of 3,4-epoxycyclohexyl methyl(meth)acrylate refined by distillation in order to remove solvents and other low boiling ingredients such as small amounts of starting materials after removing the organic peracid by extracting alone with water.

However, the neutralization before extracting the organic acid and organic peracid with water can not be applied on an industrial basis, from the view point of waste water treatments, which is described hereinabove.

The disadvantage in a product of 3,4-epoxycyclohexyl methyl(meth)acrylate is low in purity, for example, more specifically less than 90% in purity, and such unpurified 3,4-epoxycyclohexyl methyl(meth)acrylate undesirably has the tendency of readily polymerizing.

It is to be noted that there is required that the purity of the commercially available 3,4-epoxycyclohexyl methyl(meth) acrylate is from 94 to 97% by weight, and the residual components are primarily a starting material, a starting solvent and water.

JP-A-2191267 and JP-A-4217674 disclose methods for preventing coloration of 3,4-epoxycyclohexyl methyl(meth) acrylate for a long time of period. The methods relate to the addition of a decolorant and storage at a low temperature, and the addition of an anti-coloring agent, respectively.

However, even though a minor amount, additives such as the decolorant and the anti-coloring agent are fundamentally impurities for 3,4-epoxycyclohexyl methyl(meth)acrylate.

Accordingly, there should be preferably limited the unnecessary use of the additives.

Furthermore, even though the additives are employed on the way of the preparation steps, it results in that those are removed in water washing, neutralization, and evaporation step. Still further, repeated addition thereof is unpreferably troublesome, resulting in that processes only become complicated because of necessity of agitating for mixing and solid-liquid separation.

Furthermore, as a process for solving the above-described problems, the U.S. Pat. Nos. 5,382,676, 5,426,193 and 5,446,176 or EP-A-0529197 disclose a purified 3,4-epoxycyclohexylmethyl(meth)acrylate and a process for the preparation thereof comprising a combination of a plurality of steps. However, even 3,4-epoxycyclohexyl methyl(meth) acrylate prepared by the process has a disadvantage in view of coloring after there lapsed a long time of period.

From the above-described viewpoints, and as a result of studies by the present inventors, it has been found that a purified 3,4-epoxycyclohexyl methyl(meth)acrylate can be prepared by the various improved steps on a commercial basis.

SUMMARY OF THE INVENTION

An object of the present invention is to provide an improved process for the preparation of a purified 3,4-epoxycyclohexyl methyl(meth)acrylate and a stabilized 3,4-epoxycyclohexyl methyl(meth)acrylate.

A first aspect of the present invention is a process for the preparation of a purified 3,4-epoxycyclohexylmethyl(meth) acrylate from a crude reaction solution obtained by the epoxidation reaction of cyclohexenyl methyl(meth)acrylate with an organic peracid, characterized by the steps (a) to (f);

(a) washing said crude reaction solution with water to separate into an organic solution layer and an aqueous solution layer, (b) neutralizing said organic solution layer with an aqueous alkali solution to form an organic solution layer and an aqueous alkali solution layer, (c) separating said organic solution layer from said aqueous alkali solution layer, (d) evaporating said organic solution layer at temperatures ranging from 30° to 100° C. and at reduced pressures to obtain 3,4-epoxycyclohexyl methyl(meth)acrylate including low-boiling-point ingredients ranging from 3 to 50% by weight, (e) washing said 3,4-epoxycyclohexyl methyl(meth) acrylate including low-boiling-point ingredients ranging from 3 to 50% by weight with an aqueous alkali solution, and further (f) evaporating said 3,4-epoxycyclohexyl methyl(meth) acrylate including low-boiling-point ingredients ranging from 3 to 50% by weight at temperatures not more than 100° C. and at less than ½ of the reduced pressures in the above-mentioned step (d) to obtain a purified 3,4-epoxycyclohexyl methyl(meth)acrylate.

A second aspect of the present invention is a stabilized 3,4-epoxycyclohexyl methyl (meth) acrylate, wherein an amine compound is mixed in the purified 3,4-epoxycyclohexyl methyl(meth)acrylate.

BRIEF DESCRIPTION OF THE DRAWING

FIG. 1 is a flow sheet showing the steps of the present invention. In the FIG. 1, the numbers (1), (2), (3), (4), (5), (6), and (7) is a reaction vessel for epoxidation reaction, a reservoir for aging, a centrifugal extractor, a reservoir for neutralizing with an alkali solution, a first evaporator, a second evaporator, and a mixer-settler type separator, respectively.

DETAILED DESCRIPTION OF THE INVENTION

The present invention is described hereinafter in detail.

According to a first aspect of the present invention, there is provided a process for the preparation of a purified 3,4-epoxycyclohexyl methyl(meth)acrylate from a crude reaction solution obtained by the epoxidation reaction of cyclohexenyl methyl(meth)acrylate with an organic peracid, characterized by the steps (a) to (f);

(a) washing said crude reaction solution with water to separate into an organic solution layer and an aqueous solution layer, (b) neutralizing said organic solution layer with an aqueous alkali solution to form an organic solution layer and an aqueous alkali solution layer, (c) separating said organic solution layer from said aqueous alkali solution layer, (d) evaporating said organic solution layer at temperatures ranging from 30° to 100° C. and at reduced pressures to obtain 3,4-epoxycyclohexyl methyl(meth)acrylate including low-boiling-point ingredients ranging from 3 to 50% by weight, (e) washing said 3,4-epoxycyclohexyl methyl(meth) acrylate including low-boiling-point ingredients ranging from 3 to 50% by weight with an aqueous alkali solution, and further (f) evaporating said 3,4-epoxycyclohexyl methyl(meth) acrylate including low-boiling-point ingredients ranging from 3 to 50% by weight at temperatures not more than 100° C. and at less than ½ of the reduced pressures in the above-mentioned step (e) to obtain a purified 3,4-epoxycyclohexyl methyl(meth)acrylate.

The crude reaction solution which is a starting material to be used in the first aspect is prepared by the epoxidation reaction of cyclohexenyl methyl(meth)acrylate with an organic peracid.

As the organic peracid, there are exemplified performic acid, peracetic acid, perpropionic acid, m-chloroperbenzoic acid, trifuluoroperacetic acid, and perbenzoic acid.

Of the organic peracids, peracetic acid is the preferred organic peracid because it is available on an industrial basis at a moderate price and has a high stability.

Although the molar ratio of the organic peracid to cyclohexenyl methyl (meth)acrylate, more specifically to the double bond, is theoretically 1/1, the preferred range is from 0.1/1 to 10/1, more preferably from 0.5/1 to 10/1, and most preferably from 0.8/1 to 1.5/1.

If the ratio is more than 10/1, although it is preferred from the view points of the conversion of cyclohexenyl methyl (meth)acrylate to 3,4-epoxycyclohexyl methyl (meth) acrylate, a reduction of the time of period for epoxidizing and a reduction of product losses because of polymerization, resulting in disadvantages of a side reaction by the excess of the organic peracid or a reduction of selectivity of the organic peracid, and a considerable increase of the recovery cost of the peracid.

On the other hand, if the ratio is not more than 0.1/1, although it is preferred from the view points of a reduction of product losses, a reduction of the side reaction by the organic peracid and an increase of selectivity and further conversion of the organic peracid, resulting in a considerable increase of the recovery cost of cyclohexenyl methyl(meth) acrylate.

Accordingly, most preferably, a slightly excess amount of the organic peracid than the theoretical ratio is used because of a decomposition of the organic peracid, even though being small amounts, on the epoxidation reaction.

The epoxidation reaction can be preferably carried out in the presence of a solvent. The use of the solvent for dilution is effective for reducing the viscosity of the crude reaction solution and stabilizing the organic peracid, and further reducing the reaction velocity of resulting epoxy group with a resulting organic acid.

The preferred solvent includes an aromatic hydrocarbon, such as benzene, toluene, xylene, ethylbenzene, iso-propylbenzene, diethylbenzene, and p-simene, an aliphatic hydrocarbon such as cyclohexane, n-hexane, heptane, hexane, octane, nonane, decane and decaline, an alcohol such as cyclohexanol, hexanol, heptanol, octanol, nonanol and furfuryl alcohol, a ketone such as acetone, methyl ethyl ketone and cyclohexanone, an ester compound such as ethyl acetate, n-amylacetate, cyclohexyl acetate, iso-amyl propionate, and methyl benzoate, a polyvalent alcohol such as ethylene glycol, propylene glycol, ethylene glycol monomethylether, ethylene glycol monoethylether, ethylene glycol monoethylether acetate, ethylene glycol monomethylether acetate, diethylene-glycol monomethylether, diethylene glycol monoethylether an a derivative thereof, a halogenated compound such as chloroform, dimethyl chloride, carbon tetrachloride, chlorobenzene, and an ether compound such as 1,2-dimethoxyetane, etc.

For example, in case that peracetic acid is used as an organic peracid, ethyl acetate is preferably used as the solvent for dilution.

Although the molar ratio of the solvent to cyclohexenyl methyl(meth)acrylate is preferably from 0.5/1 to 5/1, more preferably from 1.5/1 to 3/1. If the ratio is less than 0.5/1, there becomes smaller the stabilizing effect to the organic peracid.

On the other hand, even though the ratio is more than 5/1, the stabilizing effect does not increase so much in comparison with an increase of costs for the recovery of the solvent.

Furthermore, in the case when the epoxidation reaction is preferably carried out, a polymerization inhibitor can be used together with a gas including molecular state oxygen.

As the gas including molecular state oxygen, air is usually employed, and it may be blown into a reaction vessel. Air may be directly blown into a liquid or into a gas space.

Although the blowing amount of air may be freely selected, too excessive amount may unpreferably cause loss of solvents.

Furthermore, in order to avoid formation of an explosive gas mixture, air is usually mixed with nitrogen.

Oxygen concentration in the mixed gas is more than 0.01% by volume, preferably more than 3% by volume.

Although higher oxygen concentration is more effective for preventing polymerization, an upper limit must be lower than concentration of an explosive limit value which is different depending upon the solvents to be employed. For example, in the case when ethyl acetate is employed as a solvent, preferred oxygen concentration is approximately 10% by volume.

As the polymerization inhibitor, there are exemplified hydroquinone, hydroquinone monomethylether, p-benzoquinone, cresol, t-butylcatecol, 2,4-dimethyl-6-t-butylphenol, 2-t-butyl-4-methoxyphenol, 3-t-butyl-4-methoxyphenol, 2,6-di-t-butyl-p-cresol, 2,5-dihydroxy-p-quinone, piperidine, ethanolamine, alpha-nitroso-beta-naphthol, diphenylamine, -phenothiazine, N-nitrosophenylhydroxylamine and N,N-diethylhydroxylamine, etc.

The polymerization inhibitor may be employed solely or in combination. The use amount of the polymerization inhibitor is preferably from 0.005 to 5%, more preferably from 0.001 to 0.1% by weight based on cyclohexenyl methyl(meth)acrylate which is a primary starting material.

Still further, a stabilizer for an organic peracid can be optionally used. As the stabilizer, there are exemplified ammonium hydrogen phosphate, potassium pyrophosphate, sodium phosphate, potassium 2-ethylhexyl pyrophosphate, sodium 2-ethylhexyl pyrophosphate, tripolyphosphoric acid, potassium tripolyphosphate, sodium tripolyphosphate, sodium 2-ethylhexyl pyrophosphate, potassium 2-ethylhexyl pyrophosphate, tetrapolyphosphoric acid, potassium tetrapolyphosphate, sodium tetrapolyphosphate, potassium 2-ethylhexyl tetrapolyphosphate, potassium 2-ethylhexyl tetrapolyphosphate, sodium 2-ethylhexyl tetrapolyphosphate, potassium hexametaphosphate and sodium hexametaphosphate, etc.

The stabilizer may be employed solely or in combination.

The use amount of the stabilizer for the organic peracid is preferably from 0.001 to 1%, more preferably from 0.01 to 0.2% by weight based on cyclohexenyl methyl(meth)acrylate which is a primary starting material, in the form of either a powder or a solution with a solvent.

The temperature region of the epoxidation reaction can be usually selected according to the reactivity of the organic peracid, that is, such that the epoxidation reaction advantageously occurs over the decomposition of the organic peracid, and further such that there does not occur the side reaction such as the opening reaction of resulting epoxy group with an organic acid derived from the organic peracid.

In the case of peracetic acid, which is the preferred organic peracid, the preferred temperature region is specifically from 0° to 70° C. In the case that the temperature is lower than 0° C., there requires a long time of period to complete the epoxidation reaction and contrarily, in the case that the temperature is higher than 70° C., there occurs decomposition of peracetic acid.

The epoxidation reaction is usually carried out at ordinary pressure conditions, and also can be optionally carried out at reduced or pressurized conditions.

And, the epoxidation reaction is carried out by a continuous process or a batchwise process.

In the case of the continuous process, there can be preferably used a piston-flow type one, in the case of the batchwise process, there can be preferably used a semi-batch type one in which the organic peracid is successively supplied.

More specifically, the starting material and the solvent are firstly supplied into a reaction vessel, and then the catalyst and the stabilizer are optionally dissolved, and then the organic peracid is successively supplied by dropwise addition as mentioned hereinabove.

The completion of the epoxidation reaction is preferably watched by monitoring the concentration of the residual organic peracid or gas chromatography analysis.

After the completion of the epoxidation reaction, first of all, the crude reaction solution is dealt with in the step (a) in order to remove the organic peracid and organic acid.

The crude reaction solution is a mixture composed of 3,4-epoxycyclohexyl methyl(meth)acrylate which is a primary product, small amounts of unreacted cyclohexenyl methyl(meth)acrylate which is a starting material, the residual organic peracid which is employed in slightly excess amounts, the organic acid derived from the reacted organic peracid, an optionally used polymerization inhibitor or a catalyst, and a solvent.

The crude reaction solution is employed, as it were, as a starting material in the first aspect of the present invention.

A centrifugal extractor or a mixer-settler type separator is preferably employed in the step (a) of the first aspect of the present invention. Furthermore, an extracting column can be also employed in the step (a).

The retention time of period while passing through the centrifugal extractor or mixer-settler type separator which has a short contacting time of period between an aqueous solution and an organic solution, is preferably adjusted in a scope within 5 minutes, and more preferably within 3 minutes depending upon a permissible loss amount of 3,4-epoxycyclohexyl methyl(meth)acrylate which is a primary product and the reaction rate between the epoxy group and the kind of the organic acid derived from the organic peracid to be employed.

The inherent minimum retention time of period depends upon a size of the centrifugal extractor, mixer-settler type separator, and extracting column to be employed.

Specifically describing, a larger sized centrifugal extractor, mixer settler type separator, and extracting column inevitably have a longer inherent minimum retention time of period.

For the purpose of further reducing the retention time of period in the case of the mixer-settler type separator, a line mixer is preferably employed in a mixing portion, and a reservoir having a smaller capacity is preferably employed in a settling portion. For the purpose of further reducing the retention time of period in the case of the extracting column, a supplying amount may be increased by the use of a column having a smaller capacity.

In the case of the centrifugal extractor, the retention time of period depends upon a continuous layer which is formed by either organic solution layer or aqueous solution layer.

In the centrifugal extractor and mixer settler type separator, an intensely-mixed degree between the organic solution layer and aqueous solution layer requires a longer time of period for separating.

Accordingly, a time of period for separating must be adjusted by a separability of the organic solution layer from aqueous solution layer.

The centrifugal extractor in which two liquids are capable of counter-currently contacting, has a rotary body or a drum integrally mounted on a rotary shaft, the rotary body or drum having a plurality of, specifically, 50 or so stages of ring members or perforated cylinders, etc.

There is assembled each stage with mixing chambers and settling chambers in the rotary body or the drum of the centrifugal extractor.

A solution to be processed initially containing a solute, and a reagent for extracting circulate counter-currently each other in the rotary body or drum, and mixing and separating operations performed in each stage allow the solute to pass into water.

In the mixing chamber, the two layers are mixed by the high relative speed between the stationary part and rotating wall.

And, in the settling chamber, the two layers previously mixed are separated by centrifugal force.

More specifically, the crude reaction solution and water which is a reagent for extracting are supplied into the rotary body or drum rotating at high speed passing through two pipes connected to a rotating shaft, respectively, and then the crude reaction solution and water are contacted at the state of a counter-current.

As the result, a heavy solution layer is radially transferred to an outside direction of the rotary body or drum by the centrifugal force, and a light solution layer is radially transferred to an inside direction of the shaft.

There can be attained the effective extraction of the organic acid and the organic peracid from the crude reaction solution by the counter-currents and transference at slits between the ring members or holes on perforated cylinders.

The organic acid and organic peracid can be extracted with water within a short retention time passing through the extractor. Extraction can be carried out within 5 minutes even in the case of two solutions having a small difference between specific gravities because of using the centrifugal force.

Although the time of period required to extract in the centrifugal extractor also depends upon the plate efficiency, the numbers of actual plate and the kinds of liquids, that is the specific gravity differences between two liquids, it is generally from several seconds to approximately 50 minutes or so.

Accordingly, in the case of the present invention, the epoxy group does not react with the organic peracid, the organic acid and water so much, resulting in only minor amounts of product losses.

It is noted that the mechanism and internal structures of such centrifugal type counter-current apparatus are specifically disclosed in U.S. Pat. Nos. 3,327,939, 3,814,307, 4,225,079, 4,272,011, 4,326,666 and 4,367,202, etc.

The step (a) is preferably carried out at relatively lower temperatures from viewpoint of preventing a reaction of 3,4-epoxycyclohexyl methyl(meth)acrylate with impurities in the crude reaction solution. Specifically, for example, the temperatures range from 0° to 50° C., preferably from 15° to 30° C., and more preferably from 15° to 25° C. However, in a too low temperature, separability unpreferably becomes poor.

Feeding ratio of water with respect to the crude reaction solution can be freely selected. Specifically, it ranges usually from 0.5/1 to 3/1 by weight, and preferably from 1/2 to 2/1 by weight, so that the amount of residual organic acid can be decreased less than 0.1% by weight, preferably less than 0.05%, and the amount of residual organic peracid can be also decreased less than 0.1%, preferably less than 0.05% by weight.

As a result of washing with water in the step (a), the crude reaction solution is separated into an organic solution layer and an aqueous solution layer in the centrifugal extractor or mixer-settler type separator, etc. to be employed, in which the organic acid and peracid are almost shifted to the aqueous solution layer.

The aqueous solution layer is separated from the organic solution layer, and then the organic solution layer is moved to a next step which is the step (b) in which neutralization is carried out with an aqueous alkali solution to form again an organic solution layer and an aqueous alkali solution layer.

As the alkalis, there are exemplified NaOH, KOH, $K_2CO_3$, $Na_2CO_3$, $NaHCO_3$, $KHCO_3$, and $NH_3$. Of those, there is preferably employed an aqueous solution of NaOH, $Na_2CO_3$, and $NaHCO_3$ from a viewpoint of separability between the organic solution layer and the aqueous alkali solution layer.

Although depending upon the concentrations of the residual organic acid and organic peracid after extraction with water, the aqueous alkali solution is employed in a concentration range of from 0.1 to 10% by weight, and preferably from 0.5 to 2% by weight.

In the case that the concentration is below 0.1% by weight, there cannot be sufficiently removed organic acids or organic peracids having high boiling points in the reaction crude solution and, contrarily, in the case that the concentration exceeds 10% by weight, there increases a load in an equipment for dealing with an aqueous alkali waste, unpreferably resulting in that an economical operation cannot be carried out.

In the neutralization step (b), the aqueous alkali solution is employed in a mixing ratio ranging from 0.1 to 5 by weight, and preferably from 0.3 to 2 by weight with respect to the organic solution layer.

In the case that the mixing ratio is below 0.1, there cannot be sufficiently removed the residual organic acid and organic peracid in the organic solution layer and, contrarily, in the case that the mixing ratio exceeds 5, it becomes problematic that there unpreferably increases a load in a water treatment equipment because of necessity of a larger reservoir.

The neutralization step (b) is preferably carried out at relatively lower temperatures from viewpoint of preventing a reaction of 3,4-epoxycyclohexyl methyl(meth)acrylate with impurities in the crude reaction solution. Specifically, for example, the temperatures range from 0° to 50° C, preferably from 15° to 30° C., and more preferably from 15° to 25° C.

However, a too low temperature condition occasionally makes the property for separating into the two solution layers lower because of an increase of the viscosity and a decrease of the gravity difference.

Although the neutralization step (b) may be carried out batchwise, it may be continuously carried out in an industrial process. In the case that it is continuously carried out, there is preferably employed a mixer-settler type equipment.

It is to be noted that the above-mentioned centrifugal counter-current extractor is unpreferably employed in the neutralization step (b) because of the short retention time of period, resulting in insufficient removal of the organic acid and peracid.

In the case of the batchwise process, an extracting column type apparatus can be preferably used.

As a result of the neutralization step (b), an organic solution layer and an aqueous solution layer are formed again in the mixer-settler type separator-or centrifugal extractor, etc. to be employed, in which the organic acid and peracid are almost shifted to the aqueous solution layer.

The organic solution layer is separated from the aqueous solution layer in the step (c).

Separation is carried out with a liquid separator such as a static decanter or a dynamic decanter such as a centrifugal extractor, and then the organic solution layer separated is supplied into the step (d).

In the step (d), the organic solution layer is evaporated at a temperature ranging from 30° to 100° C, preferably from 50° to 70° C. and at reduced pressures to obtain 3,4-epoxycyclohexyl methyl(meth)acrylate including low-boiling-point ingredients ranging from 3 to 50% by weight; and preferably from 10 to 20% by weight.

In the case that the temperature exceeds 100° C., there readily tends to cause the (co)polymerization of 3,4-epoxycyclohexyl methyl(meth)acrylate and/or cyclohexenyl methyl(meth)acrylate, even though at small amounts of the organic peracid and organic acid and, contrarily, in the case that the temperature is below 30° C., it is too low in the evaporation rate.

In the case that the low-boiling-point-ingredients are below 3% by weight, the degree of reduced pressures must be increased, unpreferably resulting in that loss of solvents increases and, contrarily, in the case that the low-boiling-point-ingredients exceed 50% by weight, evaporation in the step (f) must be carried out at a higher vacuum condition, unpreferably resulting in that there increases loss in a condenser for collecting solvents.

The organic solution layer to be supplied into the step (d) contains a mixture composed of 3,4-epoxycyclohexyl methyl(meth)acrylate which is a primary desired product, small amounts of unreacted cyclohexenyl methyl(meth)acrylate which is a starting material, the minor amounts of the organic peracid and the organic acid unremoved in the step (a) and in the neutralization step (b), a solvent which is a primary low-boiling ingredients to be evaporated, and further small amounts of by-products.

More specifically, the contents of the residual organic peracid and organic acid in the solution must be preferably reduced to the extent of less than 100 ppm, respectively.

In the case that the contents are more than 100 ppm, the epoxy group in 3,4-epoxycyclohexyl methyl(meth)acrylate reacts with the organic acid under the influence of heating in evaporation, resulting in polymerization of 3,4-epoxycyclohexyl methyl(meth)acrylate.

The evaporation is preferably carried out with an evaporator such as a thin-film evaporator. The reduced pressure in the step (d) ranges from 10 to 500 Torr depending upon the kinds of solvents to be used in the epoxidation reaction. For example, in the case that ethyl acetate is employed, it preferably ranges from 80 to 200 Torr.

Furthermore, a polyphosphoric acid compound may be preferably mixed with the organic solution layer to be supplied into the step (d).

The polyphosphoric acid compound has a chelating effect and, thereby, there is prevented polymerization by ring opening of 3,4-epoxycyclohexyl methyl (meth)acrylate because of a catalytic effect by metallic materials employed in the evaporator of the step (d).

Although the polyphosphoric acid compound is mixed as a stabilizer for the organic peracids employed in the epoxidation reaction, since it is removed together with organic acids and organic peracids in the above-described steps (a) and (b), it is preferably mixed again in the step (d).

As the polyphosphoric acid compound to be employed, there are exemplified ammonium hydrogen phosphate, potassium pyrophosphate, sodium phosphate, potassium 2-ethylhexyl pyrophosphate, sodium 2-ethylhexyl pyrophosphate, tripolyphosphoric acid, potassium tripolyphosphate, sodium tripolyphosphate, sodium 2-ethylhexyl pyrophosphate, potassium 2-ethylhexyl pyrophosphate, tetrapolyphosphoric acid, potassium tetrapolyphosphate, sodium tetrapolyphosphate, 2-ethylhexyl tetrapolyphosphate, potassium 2-ethylhexyl tetrapolyphosphate, sodium 2-ethylhexyl tetrapolyphosphate, potassium hexametaphosphate and sodium hexametaphosphate, etc. The polyphosphoric acid compound may be employed solely or in combination.

Of those, potassium pyrophosphate and esters of 2-ethylhexyl polyphosphate are preferably employed and, further, in the case that ethyl acetate is employed as a solvent in the epoxidation reaction, 2-ethylhexyl polyphosphate is most preferably employed.

Although the amount to be employed depends upon the kind of the polyphosphoric acid compound and evaporation temperature, it is preferably from 1 ppm to 10,000 ppm, more preferably from 10 to 2,000 ppm by weight based on 3,4-epoxycyclohexyl methyl(meth)acrylate.

In the case that there is employed a polyphosphoric acid compound which is a complete inorganic salt, it is low in solubility to the organic solution layer in the step (d), unpreferably resulting in that it possibly precipitates.

The polyphosphoric acid compound is removed in the step (e) which is a washing process with an aqueous alkali solution described hereinafter.

In the present invention, a bottom product in the evaporator of the step (d) is washed again with an aqueous alkali solution in the step (e). Washing with an aqueous alkali solution can be continuously carried out through a separator such as a mixer-settler type separator or centrifugal extractor.

Washing with an aqueous alkali solution in the step (e) can be carried out by the same conditions in the step (b) as described hereinabove.

As a result of washing in the step (e), an organic solution layer and an aqueous alkali solution layer are formed again, and then the solution layers are separated with a static decanter such as a mixer-settler type separator or a dynamic decanter such as a centrifugal extractor, and then the organic solution layer separated is supplied into the step (f).

In the step (f), there are nearly completely removed low-boiling-point-ingredients. The low-boiling-point-ingredients include solvents which were not intentionally removed in the step (d) and a minor amount of water which was dissolved into the organic solution layer in the step (e).

And, a range of the reduced pressures in the step (f) is essentially less than ½ of the reduced pressures in the step (d), preferably from ⅓ to ¼. Specifically, for example, in the case that ethyl acetate is employed as a solvent in the epoxidation reaction, the reduced pressures range from 5 to 250 Torr, preferably from 10 to 40 Torr.

In the case that the reduced pressures in the step (f) exceed ½ of the reduced pressures in the step (d), the low-boiling-point-ingredients cannot be removed in the product of the step (f).

The contents of the low-boiling-point-ingredients in the product of the step (f) are preferably not more than 1% by weight. If the contents exceed 1%, the product primarily including 3,4-epoxycyclohexyl methyl(meth)acrylate is not commercially available.

In the step (f), the low-boiling-point-ingredients in the product of the step (f) are evaporated at a temperature ranging from 30° to 100° C., preferably from 50° to 70° C. and at reduced pressures.

According to a second aspect of the present invention, there is provided a stabilized 3,4-epoxycyclohexylmethyl (meth)acrylate, wherein an amine compound is mixed in the purified 3,4-epoxycyclohexyl methyl(meth)acrylate.

Amine compounds may be added to the product as a stabilizer in order to prevent cationic polymerization of the product in the step (f) which is usually supplied as a commercial product.

As the amine compounds to be added, there are exemplified a primary amine, a secondary amine, a tertiary amine, and a compound which has a heterocyclic ring containing nitrogen atoms.

Of those, the tertiary amine is preferably employed.

The amine compounds may be employed solely or in combination of tertiary amines or a tertiary amine and primary or secondary amines. In the case that primary amines and/or secondary amines alone are employed, a substituent group which connects to nitrogen atom must exhibit large steric hindrance.

Because, the primary amines and/or secondary amines having a substituent group not exhibiting large steric hindrance readily react to the product which is a purified 3,4-epoxycyclohexyl methyl(meth)acrylate in the present invention, unpreferably resulting in that a hydroxyl amine is produced or the product polymerizes.

As the amine compounds to be optionally added, there are specifically exemplified a tertiary amine such as tetramethyl ethylenediamine, tetramethyl-1,3-diaminopropane, tetramethyl-1,6-hexamethylenediamine, tri-n-octylamine, tri-n-butylamine, a secondary amine such as diisopropyl amine, diisobutyl amine, N-ethylaniline, a primary amine such as 2-ethylhexylamine, 2-ethylhexyloxypropylamine, and t-butylamine, a compound which has a heterocyclic ring containing nitrogen atoms such as pyridine, picoline, pyrazine, 2-methylpyrazine, lutidine, n-methylpiperidine, and an amine-based compound such as dibutylaminopropylamine which has an intramolecular tertiary and primary amine in the molecule.

The amine compounds are employed in an amount ranging from 0.1 ppb to 20,000 ppm, preferably from 1 ppb to 10,000 ppm, more preferably from 10 ppb to 1,000 ppm, and most preferably from 10 ppb to 100 ppm.

In the case that it is below 0.1 ppb, the use of the amine compounds is meaningless and, contrarily, in the case that it exceeds 10,000 ppm, it adversely affects to the commercial product, for example, occasionally coloring.

Furthermore, it is to be noted that the amine compounds may be optionally mixed into the organic solution layers to be fed to the steps (d) and (f).

In the following, Synthesis Examples, Examples and Comparative Examples are described in order to more specifically illustrate the present invention. In the Examples, numbering of equipments corresponds to numbering in FIG. 1.

[Synthesis Example 1/Preparation of a crude reaction solution including 3,4-epoxycyclohexyl methylacrylate]

Figure 1:
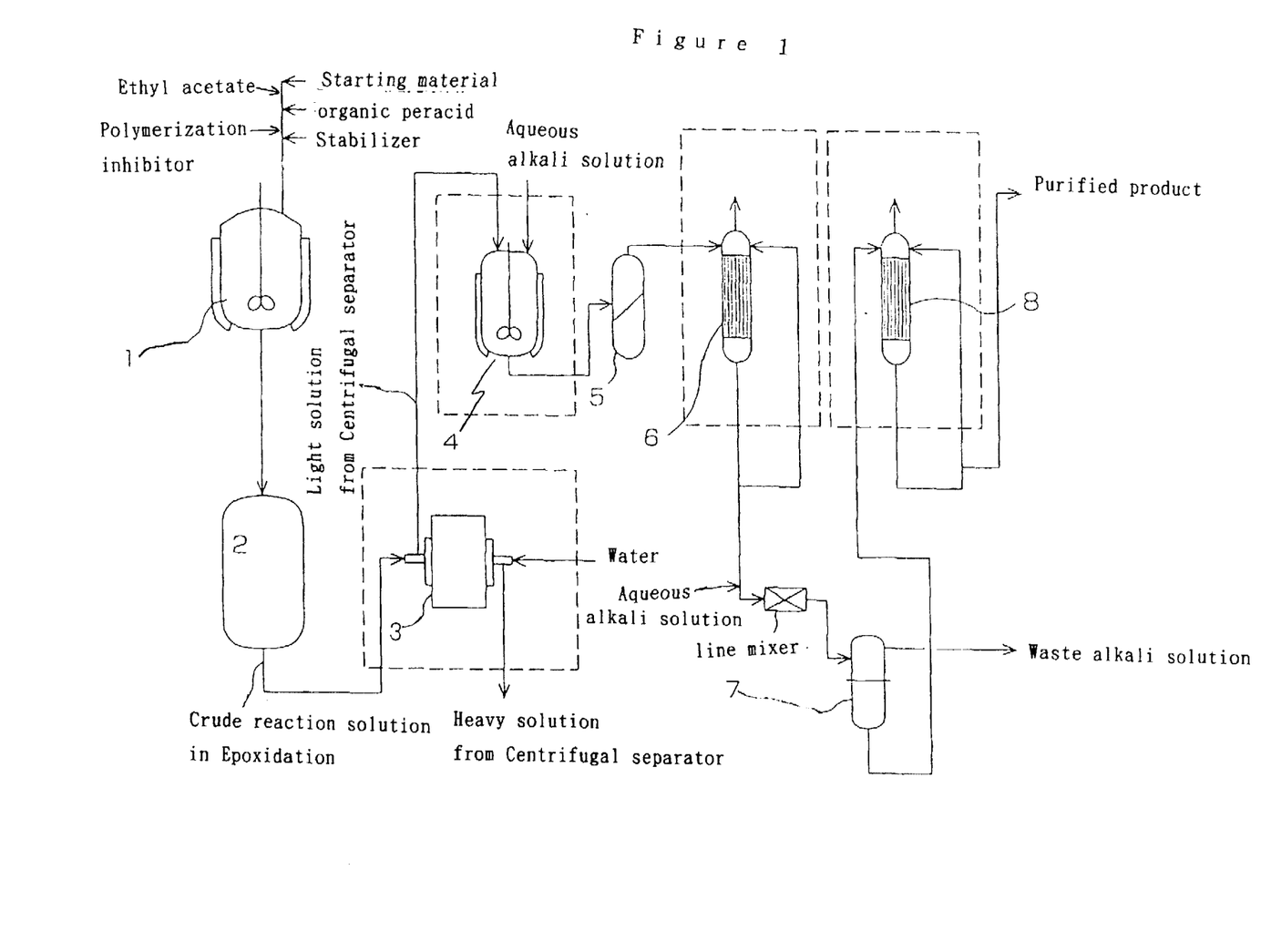

A SUS 316-made reaction vessel (1) having a capacity of 20 liter equipped with a stirrer, a tube for supplying a gas, and a jacket for cooling was charged with 3,000 parts of cyclohexenyl methylacrylate, 11,100 parts of ethyl acetate, 0.9 parts of hydroquinone monomethylether which is a polymerization inhibitor and 9.0 parts of sodium tripolyphosphate which is a stabilizer for a peracid while supplying a mixed gas composed of oxygen and nitrogen (oxygen/nitrogen=10/90 by volume) at the rate of 32 liter/hour, followed by raising the internal temperature to 40° C.

Subsequently, 5,623 parts of ethyl acetate solution including 30% of peracetic acid was added dropwise over 4 hours with a feeding volume-adjastable pump, followed by aging over 5 hours in a reservoir (2) for aging.

The internal temperature was maintained at 40° C. while adding dropwise and aging to obtain 19,723 parts of a crude reaction solution including 3,4-epoxycyclohexyl methylacrylate.

[EXAMPLE 1]

(a) washing the crude reaction solution with water:

The crude reaction solution obtained in the Synthesis Example 1 was introduced from an inlet for a light solution phase at 2108 parts/minute and water was introduced from an inlet for a heavy solution phase at 3590 parts/minute into a counter-current type centrifugal extractor (3) equipped with a rotor having an outer diameter of 46 cm and an inner diameter of 25 mm which rotates at 4000 r.p.m.

Subsequently, a light solution layer was obtained at 1664 parts/minute from an outlet for the light solution layer and a heavy solution layer was obtained at 4034 parts/minute from an outlet for the heavy solution layer.

The light solution layer was introduced again from the inlet for the light solution layer at 2108 parts/minute and water was introduced from the inlet for the heavy solution layer at 3590 parts/minute.

Subsequently, a light solution layer was obtained at 1877 parts/minute from the outlet for the light solution layer and a heavy solution layer was obtained at 3821 parts/minute from the outlet for the heavy solution layer.

The concentrations of acetic acid and peracetic acid in the light solution layer after extracting in twice with water were 400 ppm and 150 ppm, respectively.

(b) neutralizing an organic solution layer with an aqueous alkali solution and, (c) separating the organic solution layer from aqueous alkali solution layer:

A SUS 316-made reservoir (4) having a capacity of 15 liter for neutralizing with an alkali solution equipped with a stirrer and a jacket for cooling was charged with 3000 parts of the light solution layer obtained in the step (a), successively, 3000 parts of an aqueous solution including 1% of NaOH was charged into the reservoir, followed by agitating for 1 hour while maintaining the temperature at 10° C.

After settling for 5 minutes, 2790 parts of an upper (organic) solution layer was separated from a lower (aqueous) solution layer.

The concentrations of acetic acid and peracetic acid in the upper solution layer were less than 100 ppm, respectively.

(d) evaporation of organic solution layer:

Subsequently, 0.16 part of hydroquinone monomethyl-ether and 2.79 part of 2-ethylhexyl tripolyphosphate were added in 2790 parts of the upper solution layer obtained in Synthesis Example 1, the solution was supplied into a SUS-made Smith falling film type evaporator (6) maintained at the temperature of 60° C. and the reduced pressure of 150 mm Hg while supplying a mixed gas composed of oxygen and nitrogen (oxygen/nitrogen=10/90 by volume) at 32 liter/hour from the bottom of the evaporator, to which a line for discharging a liquid is connected, to obtain a solution including 5% of low-boiling-point ingredients.

(e) washing with an aqueous alkali solution:

The solution obtained was washed with an aqueous alkali solution containing NaOH of 1% at the mixing ratio of 1/1 by volume in a mixer-settler type separator (7) composed of a static mixer and a reservoir for an alkali solution.

As a result of the step (e), an organic solution layer and an aqueous solution layer were formed again in the mixer-settler type separator. The organic solution layer was separated from the aqueous solution layer.

(f) evaporating at less than ½ of the reduced pressures in the step (d):

The organic solution layer separated was supplied into a SUS-made Smith falling film type evaporator (8) maintained at the temperature of 60° C and the reduced pressure of 40 mm Hg while supplying a mixed gas composed of oxygen and nitrogen (oxygen/nitrogen=10/90 by volume) at 32 liter/hour from the bottom of the evaporator, to which a line for discharging a liquid is connected, to obtain 538 g of a product in the bottom of the evaporator. Color hue of the product was measured im mediately after taken out of the evaporator, 2 months after, 3 months after, and 5 months after, respectively.

It is to be noted that the product was not gelled even in 5 months after. Results are shown in Table 1.

[Comparative Example 1]

The same procedures were followed as in Example 1, except that the step (e) was not carried out.

Results are shown in Table 1.

[Comparative Example 2]

The same procedures were followed as in Comparative Example 1, except that the wiped film evaporator was employed in place of a falling film evaporator.

Results are shown in Table 1.

[Comparative Example 3]

The same procedures were followed as in Comparative Example 1, except that the wiped film evaporator was employed in place of the falling film evaporator, and a product taken out of the evaporator in the step (f) was treated by absorption method with a hydrotalcite compound (Kyoward manufactured by Kyowa Kagaku Kogyo, Ltd.). APHA value changed from 200 to 55 by absorption.

TABLE 1

|  | (A) | (B) | (C) | (D) |
|---|---|---|---|---|
| Example 1 | 30 | 65 | 65 | 80 |
| Comparative Example 1 | 50 | 100 | 100 | 140 |
| Comparative Example 2 | 80 | 120 | 120 | 130 |
| Comparative Example 3 | 55 |  |  | 85 |

In the Table 1, (A), (B), (C), and (D) are the values of APHA in immediately after being taken out of the evaporator, 2 months after, 3 months after, and 5 months after, respectively.

[Comparative Example 4]

The same steps (a), (b), (c), and (d) were followed as in Example 1, except 2-ethylhexyl tripolyphosphate was not added in the step (d) to obtain a product from the evaporator.

Thin layer was formed over the surface of the product taken out of the evaporator at 2 hours after, and the product was nearly completely gelled at 6 hours after.

[EXAMPLE 2]

50 ppb of tetramethyl ethylenediamine was mixed with the product obtained in Example 1, and then heating test was carried out at 60° C. to measure a stability.

Results are shown in Table 2.

[Comparative Example 5]

The same procedures were followed as in Example 2, except tetramethyl ethylenediamine was not mixed.

Results are shown in Table 2.

TABLE 2

|  | (A) | (B) | (C) |
|---|---|---|---|
| Example 2 | 100 | 100 | 99.2 |
| Comparative Example 5 | 100 | 95.9 | 90.9 |

In the Table 2, (A), (B), and (C) are transmittance (%) of a light having the wave length of 580 nm in immediately after mixing, 13 days after, and 27 days after, respectively.

[EXAMPLE 3]

10 ppm of tetramethyl ethylenediamine was mixed with the product obtained in Example 1, and then heating test was carried out at 80° C. to measure a stability.

Results are shown in Table 3.

[Comparative Example 6]

The same procedures were followed as in Example 3, except tetramethyl ethylenediamine was not mixed.

Results are shown in Table 3.

TABLE 3

|  | (A) | (B) | (C) |
|---|---|---|---|
| Example 3 | 95.2 | 95.2 | 95.1 |
| Comparative Example 6 | 95.2 | 91.0 | 86.5 |

In the Table 3, (A), (B), and (C) are transmittance (%) of a light having the wave length of 580 nm in immediately after mixing, 1 hour after, and 2 hour after, respectively.

[EXAMPLE 4]

1 ppm of tetramethyl ethylenediamine was mixed with the product obtained in Example 1, and then heating test was carried out at 60° C. to measure a stability.

Result are shown in table 4.

[Comparative Example 7]

The same procedures were followed as in Example 4, except tetramethyl ethylenediamine was not mixed.

Results are shown in Table 4.

TABLE 4

|  | (A) | (B) | (C) |
|---|---|---|---|
| Example 4 | 100.0 | 99.9 | 99.9 |
| Comparative Example 7 | 100.0 | 98.5 | 95.9 |

In the Table 4, (A), (B), and (C) are transmittance (%) of a light having the wave length of 580 nm in immediately after mixing, 4 hour after, and 8 hour after, respectively.

While the invention has been described in detail and with reference to specific embodiments thereof, it will be apparent to one skilled in the art that various changes and modifications can be made therein without departing from the spirit and scope thereof.

What is claimed is:

1. A process for the preparation of a purified 3,4-epoxycyclohexyl methyl(meth)acrylate from a crude reaction solution obtained by the epoxidation reaction of cyclohexenyl methyl (meth)acrylate with an organic peracid, characterized by the steps (a) to (f);

(a) washing said crude reaction solution with water to separate into an organic solution layer and an aqueous solution layer, (b) neutralizing said organic solution layer with an aqueous alkali solution to form an organic solution layer and an aqueous alkali solution layer, (c) separating said organic solution layer from said aqueous alkali solution layer, (d) evaporating said organic solution layer at temperatures ranging from 30° to 100° C. and at reduced pressures to obtain 3,4-epoxycyclohexyl methyl(meth)acrylate including low-boiling-point-ingredients ranging from 3 to 50% by weight, (e) washing said 3,4-epoxycyclohexyl methyl(meth)acrylate including low-boiling-point-ingredients ranging from 3 to 50% by weight with an aqueous alkali solution, and further (f) evaporating said 3,4-epoxycyclohexylmethyl(meth)acrylate including low-boiling-point-ingredients ranging from 3 to 50% by weight at temperatures not more than 100° C. and at less than ½ of the reduced pressures in the above-mentioned step (d) to obtain a purified 3,4-epoxycyclohexyl methyl(meth)acrylate.

2. A process as set forth in claim 1, wherein a polyphosphate compound is mixed into the organic layer before said step (c).

3. A process as set forth in claim 1, wherein said organic peracid is peracetic acid.

4. A process as set forth in claim 1, wherein a centrifugal extractor or a mixer-settler type separator is employed in said step (a).

5. A process as set forth in claim 1, wherein a centrifugal extractor or a mixer-settler type separator is employed in said step (d).

6. A process as set forth in claim 1, wherein a flash evaporator is employed in said step (c) and said step (e).

7. A stabilized 3,4-epoxycyclohexyl methyl(meth)acrylate, wherein an amine compound is mixed in said 3,4-epoxycyclohexyl methyl(meth)acrylate.

8. A stabilized 3,4-epoxycyclohexyl methyl(meth)acrylate as set forth in claim 7, wherein said amine compound is a tertiary amine.

9. A stabilized 3,4-epoxycyclohexyl methyl(meth)acrylate as set forth in claim 8, wherein said tertiary amine is tetramethyl ethylenediamine.

* * * * *